United States Patent [19]

Chanavaz

[11] Patent Number: 5,205,746
[45] Date of Patent: Apr. 27, 1993

[54] SURGICAL IMPLANT FOR ORAL AND MAXILLOFACIAL IMPLANTOLOGY

[75] Inventor: Manuel Chanavaz, Rouen, France

[73] Assignee: Societe de Fabrication de Materiel Orthopedique - Sofamor, Paris, France

[21] Appl. No.: 913,991

[22] Filed: Jul. 17, 1992

Related U.S. Application Data

[63] Continuation of Ser. No. 638,868, Jan. 11, 1991, abandoned.

[30] Foreign Application Priority Data

Jan. 11, 1990 [FR] France .................. 9000283

[51] Int. Cl.⁵ .................................... A61C 8/00
[52] U.S. Cl. ..................................... 433/174
[58] Field of Search ...................... 433/172, 173, 174

[56] References Cited

U.S. PATENT DOCUMENTS

| | | | |
|---|---|---|---|
| 3,579,831 | 5/1971 | Stevens | 433/174 |
| 3,589,011 | 6/1971 | Sneer | 433/174 |
| 4,713,004 | 12/1987 | Linkow | 433/174 |
| 4,826,434 | 5/1989 | Krueger | 433/174 |
| 4,854,872 | 8/1989 | Detsch | 433/173 |
| 4,872,839 | 10/1989 | Brajnovic | 433/173 |
| 4,904,187 | 2/1990 | Zingheim | 433/173 |
| 4,995,810 | 2/1991 | Söderberg | 433/141 |
| 5,000,686 | 3/1991 | Lazzara et al. | 433/174 |
| 5,061,181 | 10/1991 | Niznick | 433/174 |
| 5,076,788 | 12/1991 | Niznick | 433/173 |

FOREIGN PATENT DOCUMENTS

| | | |
|---|---|---|
| 0170818 | 2/1986 | European Pat. Off. . |
| 323559 | 7/1989 | European Pat. Off. ............ 433/174 |
| 0343135 | 11/1989 | European Pat. Off. . |
| 3828013 | 2/1990 | Fed. Rep. of Germany ...... 433/174 |
| 2571607 | 4/1986 | France . |
| 8803007 | 5/1988 | PCT Int'l Appl. ................. 433/174 |

Primary Examiner—Robert P. Swiatek
Assistant Examiner—Cindy A. Cherichetti
Attorney, Agent, or Firm—Wenderoth, Lind & Ponack

[57] ABSTRACT

This implant comprises a body (1) consisting of a smooth head (2) and of a cylindrical rod (3) threaded over the whole of its length, and whose end (13) is rounded, straight longitudinal grooves moreover being made starting from the rounded end (13) over part of the length of the threaded rod (3), and one or several diametral transverse holes (15) being formed at the halfway point or a lower point of the body (1) of the implant; these features permit a more intimate immobilization of the implant with the osseous elements in the bone socket (alveolus), and they contribute to limiting the compression of the bone and therefore oppose its becoming brittle through demineralization; the undestroyed osseous debris is collected in the grooves (14) and in the hole (15), which thus permits an ossification and a transvascularization the implant, the hole (15) moreover limiting the dehiscence of the bone from its smooth head (2).

11 Claims, 1 Drawing Sheet

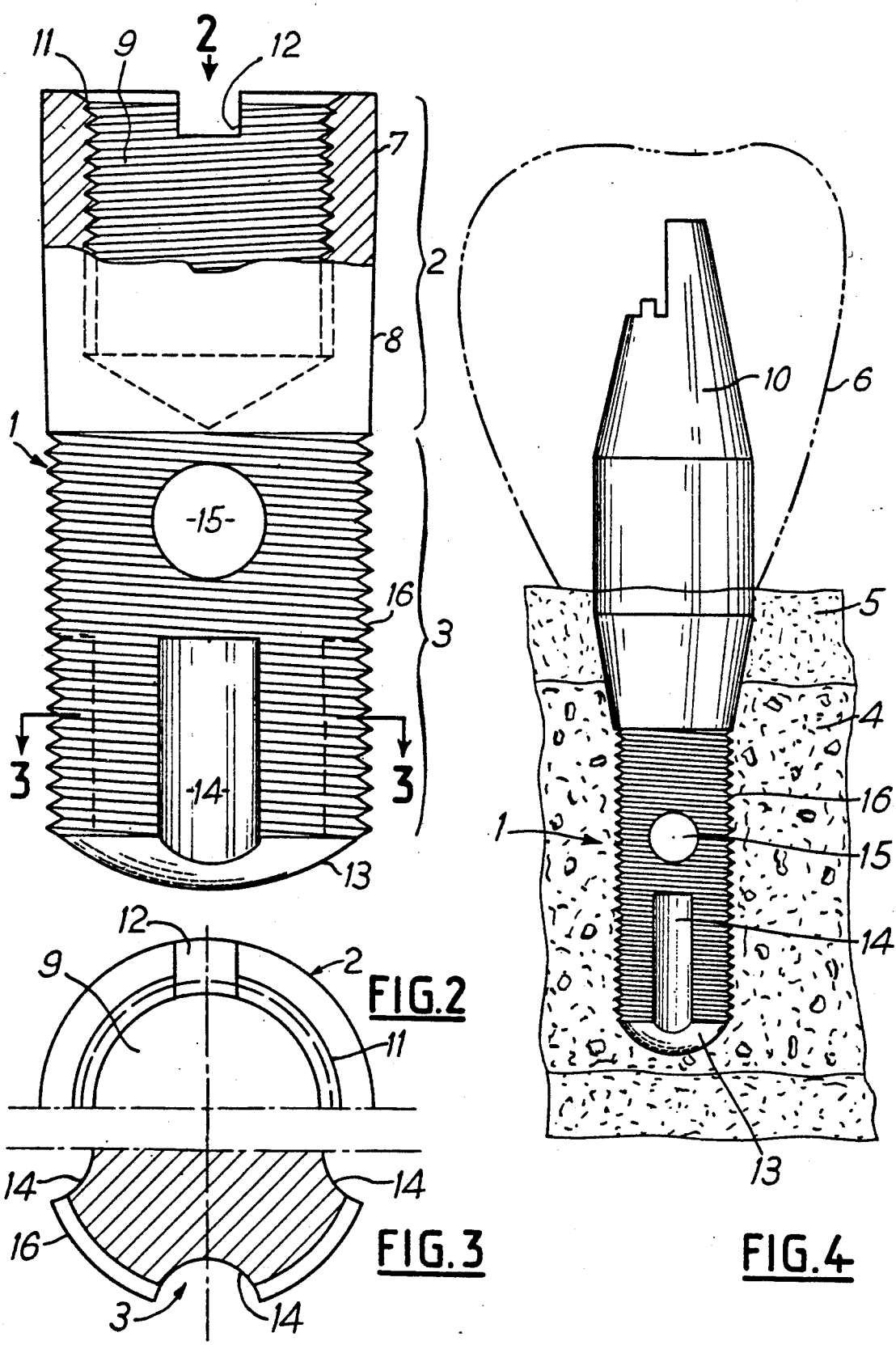

SURGICAL IMPLANT FOR ORAL AND MAXILLOFACIAL IMPLANTOLOGY

This application is a continuation of now abandoned U.S. patent application Ser. No. 07/638,868 filed on Jan. 11, 1991.

The present invention relates to a surgical implant for multidiscipline use, intended for oral and maxillofacial implantology, that is to say dental, orbito-ocular, nasal, auricular implantology, etc.

Various embodiments of oral implants are known, these generally comprising a tubular body consisting of a smooth head and a cylindrical or cylindro-conical rod intended to be screwed or inserted by compaction into an osseous volume drilled beforehand using a tap.

These implants, normally made of titanium, then receive a so-called "post-implant" element which constitutes a pillar or stump serving as a support for a prosthetic superstructure, for example a tooth. The rod is not threaded over its entire length and is finished with a smooth narrowed end, for example conical, in order to facilitate penetration of the implant into the osseous mass. The end of the implant therefore causes trauma, which reduces the scope of use of these implants. Indeed, in certain sensitive areas in maxillofacial surgery, the presence of this "sharp edge" could cause serious damage, such as severing a nerve or puncturing the sinusal mucosa, so that these implants have a limited field of use.

In addition, after a few years following the implantation, a dehiscence or packing of the bone over part of the length of the implant and all around the latter is generally observed. Moreover, the compression of the bone surrounding the implant causes a lowering of the pH of the osseous mass, and this increase in acidity in turn results in a decrease in the calcium content of the bone, which makes the latter brittle.

Finally, the conical end part of the known implants limits the compression of the bone in this site, and thus counters a local lowering of the pH of the bone, but in contrast lessens the stability of the connection and of the fastening of the implant in the osseous plate. It is for this reason that a transverse perforation is made at the end of the implant, which perforation permits blood irrigation directly on both sides of the implant and thus a supplementary transvascularization via the bridge formed in this way. However, this transverse perforation near the end of the body of the implant does not permit limiting the compression of the bone over the greater part of the body of the implant, and thus the increase in acidity and the resulting decrease in the calcium content of the bone.

The aim of the present invention is therefore to provide an implant which does not have these various disadvantages.

According to the invention, the cylindrical rod of the body of the implant is threaded over the whole of its length.

Compared to the previously known implants, the fact that the threading is extended up to the apical end ensures a more intimate connection of the implant with the bone socket or "alveolus". The medullary debris of the bone produced during the drilling and tapping operations lodge passively (not compressed) in the threaded and hollowed-out spaces and play a not inconsiderable osteoconduction role, which makes it possible to obtain a more complete immobilization of the implant.

According to another characteristic of the implant according to the invention, at least two longitudinal grooves, for example four, are formed externally over part of the length of the threaded rod, these grooves (indentation notches) being situated in the apical half-length of said threaded rod.

These external longitudinal grooves or indentation notches constitute real cicatricial chambers for accommodating the osseous debris which is not expelled by tapping of the bone socket and screwing of the implant, thus making possible an ossification which ensures a more intimate connection and a complete integration of the implant with the medullary bone.

Other features and advantages of the invention will emerge from the following description in which reference is made to the attached drawings which illustrate one embodiment by way of a non-limiting example.

FIG. 1 is a longitudinal elevation view, on an enlarged scale, of an embodiment of the oral implant according to the invention.

FIG. 2 is a partial plan view of the implant in FIG. 1.

FIG. 3 is a partial transverse section along 3—3 in FIG. 1.

FIG. 4 is an elevation view, on an enlarged scale, of the implant in FIG. 1 integrated in a maxillary osseous volume, topped by a pillar for supporting an artificial tooth.

The oral surgical implant shown in FIGS. 1 and 2 is intended for osteo-integrated maxillofacial, dental, orbito-ocular, nasal and auricular implantology. In other words, this implant can be used for the maxillary sinuses, the nasal fossae and the pterygoid regions.

This implant comprises a body 1 consisting of a smooth head (neck) 2 intended to be situated in the mucoperiosteal (periodontal) region, and of a threaded rod 3 intended to be screwed into a bone socket, in order to be topped with a prosthetic superstructure.

In the dental application as shown in FIG. 4, the body 1 is osteo-integrated to an osseous plate 4 and is topped by a superstructure consisting of a pillar or "post-implant" on which an artificial tooth 6 is fixed.

The head 2 comprises a first cylindrical end zone 7, which is coronal or mucoperiosteal (periodontal) or percutaneous depending on the intended use, followed by a second conical zone 8. The zone 7 is called "coronal" by analogy with the natural form of a tooth which comprises an end corresponding to the dental crown, while the other end, again by the same analogy, recalls the apical end of the root. These zones are smooth, the cylindrical part 7 having a length of 1 mm, for example. A tapped hole 9 is made in the head 2, optionally with a bevel or countersink 11, and two diametrically opposed grooves 12, not opening to the outside, are arranged in the cylindrical zone 7. As a numerical example, these grooves 12 can have a width of 1 mm and a depth of 0.5 mm.

Beyond the conical part 2, the body 1 consists of a rod 3 provided with a thread 16 over the whole of its length and whose end opposite the head 2 is extended by a rounded end part 13, for example semi-spherical.

At least two external and diametrally opposed longitudinal grooves 14, for example six, which are separated at equal angular intervals (FIG. 3), are formed on the threaded rod 3 starting from the base of its rounded dome 13 and over part of the length of the rod 3, for example half of this length. Finally, substantially at the half-way point, or at a lower point towards the grooves 14, the body 1 is pierced with one or several diametral transverse holes 15. The thread 16 extends over the greater part of the length of the body 1, and the hole 15 passes through the threaded rod 3.

The use and the technical advantages of the implant which has just been described are as follows.

The bone socket is formed using a set of instruments suitable for osteo-integrated oral implantology, after which the surgeon puts the chosen implant into position. This positioning is carried out by means of perforating, tapping and screwing the body 1 into the bone socket with the aid of a so-called "implant transfer" tool. More precisely, and taking into account that the diameter of the threaded rod 3 is slightly greater than the diameter of the bone socket, for example 0.1 mm, the screwing constitutes an actual tapping, which results in the close contact of the bone with the implant, and the provision of fresh undestroyed osseous debris due to the tapping. This debris can add to the existing debris resulting from the preceding phases in the working of the bone socket, and it lodges in the grooves 14 as well as in the hole 15, as already indicated. By permitting the ossification and a more intimate connection of the bone and the implant, the debris is the initiator of the new bone.

It is thus possible to avoid, firstly, a lateral or radial compression and, secondly, a longitudinal compression of the bone when the implant is in its final position, by virtue of the rounded end 13. The conditions of non-compression of the peripheral bone are therefore not met upon completion of the positioning of the implant.

The rounded end 13 of the implant fulfills two functions: on the one hand, it facilitates the passage, by sliding, of the osseous debris from the bottom of the bone socket toward the straight grooves 14 and, consequently, the subsequent ossification in the latter, as well as in the transverse hole 15, by neo-vascularization; on the other hand, it prevents any traumatic damage or any possible fracturing of the osseous tables in the very sensitive regions (nasal fossae, sinusal cavity, regions in contact with a nerve) by raising the membrane covering this region instead of possibly severing a nerve by means of a sharp edge, or irreversibly puncturing a sinusal membrane.

Given the presence of osseous debris at the bottom of the socket, on the lateral parts of the implant and in the transverse hole 15, the mechanisms for osseous stimulation can then begin and generate neo-vascularization.

Another important function of the longitudinal grooves 14 lies in the fact that they limit the compression of the bone, thus the lowering of its pH, and consequently its demineralization, and the resulting brittleness of the bone.

The transverse hole 15 (or holes 15) has a double function:

a) on the one hand, it permits blood irrigation, that is to say the transvascularization of the body 1 without passing via its circumference. It thus contributes locally to maintaining the physiological equilibrium of the blood pH. It therefore counters the corresponding increase in acidity of the bone in this zone, and thus its becoming brittle. The blood passage in the hole 15 thus returns the pH and the calcium content of the bone to normal. This transvascularization also promotes the genesis of a bone "cortex" through the hole, which contributes to the blocking (or natural wedging) of the implant by rotation in the bone socket;

b) on the other hand, it limits the progress of the dehiscence or resorption of the bone from the head 2, as is found in all the known implants after a period of the order of 5 to 7 years, by maintaining an osseous zone protected in the hole 15.

The centro-medullary perforation formed by the hole (or holes) 15 is thus an element combating the osseous destruction around the implant, as well as an element for its biomechanical reinforcement.

The smooth head 2 forming the upper part of the implant, (mucoperiosteal part) is situated, once the implant is in position, in the half-osseous and half-mucous region (osseous 4 and mucous 5 plate, FIG. 2 [sic]). The cylindro-conical configuration of the head 2 avoids a damaging compression of the cortical bone at the time of osteotomy, as well as a complete penetration of the head 2 into the bone. The cone 8 permits on the one hand a good adaptation to the soft tissues ("periodontal" implant neck) and on the other hand a slowing-down of the resorption of the osseous plate. Indeed, in the absence of the conical part 2, the smooth cylindrical zone 7 can result in a resorption of the osseous mass in contact with the mucoperiosteal part of the implant. This smooth zone also permits maintaining of good periodontal hygiene.

Once the implant has been put into position and integrated in the osseous plate, it is possible to fix it there by screwing in the tapped hole 9 the stump 10 or post-implant which is to constitute the pivot of a prosthetic superstructure, such as the tooth 6.

In a manner known per se, the implant can be made of pure titanium or of titanium alloy. A number of variations can be made to the embodiment described: for example, the rounded end 13 can be more or less pronounced. The grooves 12 can be omitted, in order to permit the fitting of post-implants already available on the market. Thus, the grooves 12 can be replaced by any type of impression permitting the screwing of the implant (hexagonal, star-shaped, etc.). The design of the implant according to the invention makes it possible to reduce its diameter compared to the known implants, which is advantageous for those regions where the osseous volume has a small thickness.

What is claimed is:

1. A surgical implant for osteo-integrated maxillo-facial implantation, comprising a longitudinal body which consists of a cylindrical rod having a substantially uniform diameter along its length, said cylindrical rod having a rounded end portion at the apical end of said rod, a smooth head portion at the other end of said rod, and a threaded portion between said rounded end portion and said smooth head portion, said cylindrical rod being threaded over the entire length of said threaded portion, said rod having at least two longitudinal grooves formed externally on said rod and extending from a point within said rounded end portion to a point within said threaded portion of said rod, and said rod being pierced with at least one diametral transverse hole at a point substantially midway along the length of said rod within said threaded portion of said rod.

2. A surgical implant for osteo-integrated maxillo-facial implantation, comprising a longitudinal body which consists of a cylindrical rod having a substantially uniform diameter along its length, said cylindrical rod having a rounded end portion at the apical end of said rod, a smooth head portion at the other end of said rod, and a threaded portion between said rounded end portion and said smooth head portion, said cylindrical rod being threaded over the entire length of said threaded portion, said rod having at least two longitudinal grooves formed externally on said rod and extending from a point within said rounded end portion to a point within said threaded portion of said rod, and said rod being pierced with at least one diametral transverse hole at a point offset from the midway point of said rod towards the apical end of said rod within said threaded portion of said rod.

3. An implant according to claim 1 or 2, wherein said smooth head portion of said body comprises a first cylindrical end zone and a second cylindrical zone, said second cylindrical zone connecting said rod to said first cylindrical end zone.

4. An implant according to claim 3 wherein said first cylindrical end zone is coronal.

5. An implant according to claim 3 wherein said first cylindrical end zone is mucoperiosteal.

6. An implant according to claim 3, wherein said first cylindrical end zone is percutaneous.

7. An implant according to claim 1 or 2, wherein said longitudinal grooves extend approximately half the length of said rod.

8. An implant according to claim 1 or 2, wherein said rounded end portion is semi-spherical.

9. An implant according to claim 1 or 2, wherein said terminal end of said first cylindrical end zone has a cavity which is internally threaded for engagement with a pillar for supporting a prosthetic member.

10. An implant according to claim 1 or 2, wherein said rod is pierced with a plurality of diametral transverse holes between the apical end and the midway point of said rod.

11. An implant according to claim 1 or 2, wherein said rod has between three and six longitudinal grooves formed externally on said rod separated at equal intervals and extending from said rounded end portion of said rod.

* * * * *